United States Patent [19]

Wong et al.

[11] Patent Number: 5,302,721

[45] Date of Patent: Apr. 12, 1994

[54] METHOD OF PREPARATION OF PHYSOSTIGMINE CARBAMATE DERIVATIVES FROM ESERETHOLES

[75] Inventors: George S. K. Wong, Summit; Thomas B. K. Lee, Whitehouse Station; Franz J. Weiberth, Belle Mead, all of N.J.

[73] Assignee: Hoechst-Roussel Pharmaceuticals Incorporated, Somerville, N.J.

[21] Appl. No.: 918,337

[22] Filed: Jul. 21, 1992

[51] Int. Cl.$^5$ ............................................. C07D 487/04
[52] U.S. Cl. ...................................................... 548/429
[58] Field of Search ................... 546/147; 548/427, 429

[56] References Cited

PUBLICATIONS

March, *Advanced Organic Chemistry*, 3rd Edition, 1989; p. 371.

*Primary Examiner*—C. Warren Ivy
*Assistant Examiner*—Zinna N. Davis
*Attorney, Agent, or Firm*—Barbara V. Maurer

[57] ABSTRACT

This application relates to a new process for the preparation of a product of the formula

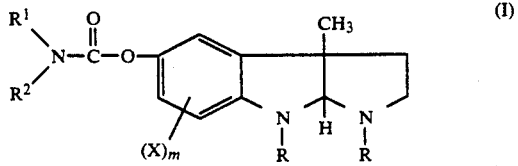

wherein
  R is loweralkyl;
  $R^1$ is hydrogen, loweralkyl, lowercycloalkyl, lowercycloalkylloweralkyl, lowerbicycloalkyl, aryl or arylloweralkyl;
  $R^2$ is loweralkyl, lowercycloalkyl, lowercycloalkylloweralkyl, lowerbicycloalkyl, aryl or arylloweralkyl; or
  $R^1$ and $R^2$ taken together with the nitrogen atom to which they are attached from a 3,4-dihydro-2H(1H)-isoquinoline group;
  X is loweralkyl, loweralkoxy, halogen or trifluoromethyl; and
  m is 0, 1 or 2;
which process comprises
  (a) contacting a compound of formula II

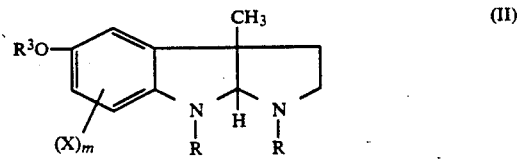

wherein R, X and m are as defined above and $R^3$ is loweralkyl, with aluminum chloride followed by tartaric acid
to afford a compound of formula III

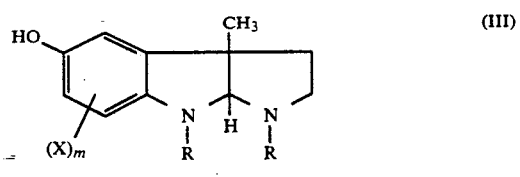

wherein R, X and m are as defined above;
  (b) contacting the reaction mixture containing the compound of Formula III either
  (1) with an isocyanate of the formula $R^1NCO$ and obtaining a product of the formula I wherein $R^2$ is hydrogen; or
  (2) with a compound of formula IV

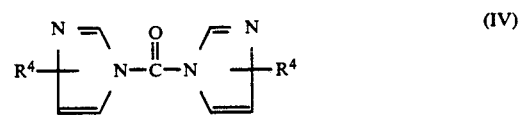

wherein $R^4$ is hydrogen or loweralkyl in the presence of a carboxylic acid of the formula $R^5COOH$ (Abstract continued on next page.)

wherein $R^5$ is loweralkyl to afford a compound of formula V
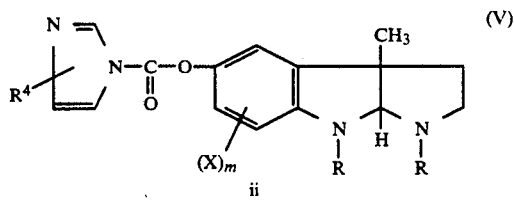
wherein R, $R^4$, X and m are as above;
contacting the reaction mixture containing the compound of Formula V with a compound of the formula
$R^1R^2NH$
wherein $R^1$ and $R^2$ are as above; and
isolating the product of Formula I.
14 Claims, No Drawings

METHOD OF PREPARATION OF PHYSOSTIGMINE CARBAMATE DERIVATIVES FROM ESERETHOLES

This application relates to a new process for the preparation of a product of the formula

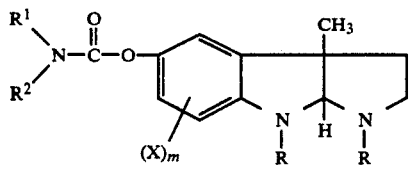

wherein
R is loweralkyl;
R¹ is hydrogen, loweralkyl, lowercycloalkyl, lowercycloalkylloweralkyl, lowerbicycloalkyl, aryl or arylloweralkyl;
R² is loweralkyl, lowercycloalkyl, lowercycloalkylloweralkyl, lowerbicycloalkyl, aryl or arylloweralkyl; or
R¹ and R² taken together with the nitrogen atom to which they are attached from a 3,4-dihydro-2(1H)-isoquinoline group;
X is loweralkyl, loweralkoxy, halogen or trifluoromethyl; and
m is 0, 1 or 2;
which process comprises
(a) contacting a compound of formula II

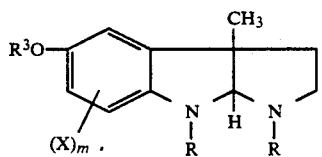

wherein R, X and m are as defined above and R³ is loweralkyl, with aluminum chloride followed by tartaric acid to afford a compound of formula III

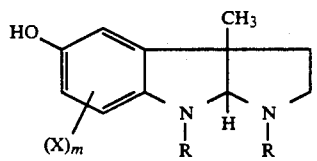

wherein R, X and m are as defined above;
(b) contacting the reaction mixture containing compound of Formula III either
(1) with an isocyanate of the formula R¹NCO and isolating a product of the formula I wherein R² is hydrogen; or
(2) with a compound of formula IV

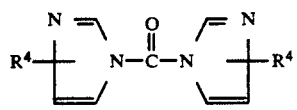

wherein R⁴ is hydrogen or loweralkyl in the presence of a carboxylic acid of formula

R⁵COOH wherein R⁵ is loweralkyl to afford a compound of formula V

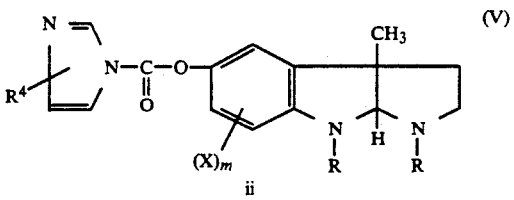

wherein R, R⁴, X and m are as above;
contacting the reaction mixture containing compound of Formula V obtained in step (b) with a compound of formula

R¹R²NH wherein R¹ and R² are as above; and
isolating the product of Formula I.

The products are useful as memory-enhancing and analgesic agents.

Unless otherwise stated or indicated, the term loweralkyl means a straight or branched alkyl group having from 1 to 6 carbon atoms. Examples of alkyl include methyl, ethyl, n-propyl, iso-butyl, pentyl, and hexyl.

Unless otherwise stated or indicated, the term cycloalkyl means a saturated ring containing 3 to 7 carbon atoms. Examples of cycloalkyl include cyclopropyl, cyclohexyl and cylcoheptyl.

Unless otherwise stated or indicated, the term bicycloalkyl means a group having from 7 to 11 carbons.

Unless otherwise states or indicated, the term halogen means fluorine, chlorine, bromine or iodine.

Unless otherwise stated or indicated, the term aryl means an unsubstituted phenyl or aromatic heterocyclic group; or a phenyl or aromatic heterocyclic group substituted with 1, 2 or 3 substituents each of which being independently loweralkyl, loweralkoxy, halogen, hydroxy, trifluoromethyl, phenoxy or benzyloxy.

Other methods for preparation of physotigmine carbamate derivatives are known. See for example Hamer, U.S. Pat. No. 3,791,107, and Brufani, U.S. Pat. No. 4,831,155. However, there remains a need for higher yield and/or less costly means for obtaining these compounds.

The process of this invention provides a less expensive starting material. In a preferred embodiment it also provides for a more convenient "one-pot" process wherein the intermediates are not isolated, thus avoiding the expense, time and yield of isolating the intermediate compounds.

It has been found that the reaction to form the compound of Formula III from the compound of Formula II, preferably wherein X is hydrogen, R is methyl and R³ is methyl or ethyl, is advantageously carried out using an agent such as aluminum chloride, hydrobromic acid or boron tribromide, preferably aluminum chloride. Generally, the reaction is carried out in an organic solvent such as petroleum ether or dichloroethane, preferably dichloroethane, at a temperature of from about 0° C. to about 100° C., preferably from about 10° C. to about 80° C. The mixture is then poured into ice and water or acid such as hydrochloric acid.

The pH is then adjusted to from about 5 to about 10, preferably from about 8 to about 9 by addition of base such as sodium hydroxide, potassium hydroxide or potassium carbonate, An equivalent (based on AlCl$_3$) of an organic acid such as tartaric acid maybe optionally added at pH 6 to 7 to solubilize the aluminum salts before the final pH adjustment to 8-9. The eseroline (II) is extracted into an organic solvent such as ethyl acetate, dichloroethane or methylene chloride and the resulting solution is dried with anhydrous potassium carbonate or molecular sieves.

Then to the dried solution containing eseroline (III) is added either an alkyl isocyanate or substituted alkyl isocyanate to form the compound of Formula I (wherein R$^3$ is hydrogen) or a carbamoylating agent such as carbonyldiimidazole, wherein the pH is within the range of about 4.0 to about 13.0 to form the compound of Formula V.

In the case where an alkyl isocyanate is added to form the compound of Formula I, the reaction temperature is generally between about 0° C. and about 25° C., preferably about 5° C. to about 10° C. The reaction is monitored and the pH is maintained between about 9 and 10 by the addition of a base such as, for example, potassium t-butoxide or an acid such as, for example, acetic acid.

In the case where carbonyldiimidazole is added to form the compound of Formula V, the addition is carried out at from about 0° C. to about 25° C., preferably at about 20° C., preferably in the presence of a carboxylic acid, such as for example, acetic acid.

The reaction mixture containing the compound of Formula V is then preferably acidified to a pH from about 4.5 to about 6, more preferably to about 5.2 with an acid, such as for example acetic acid, and an amine such as tetrahydroisoquinoline is added to give the compound of Formula I in good yields.

The addition of the amine is generally carried out from about −15° C. to about 25° C., preferably at from about −10° C. to about 20° C.

The following examples are for illustration purposes only and are not to be construed as limiting the invention. All temperatures are given in degrees centigrade (°C.) unless otherwise indicated.

EXPERIMENTAL

EXAMPLE 1

(3aS-cis)-1,2,3a,8,8a-Hexahydro-1,3a,8-trimethylpyrrolo[2,3-b]-indol-5-yl 3,4-dihydro-2(1H)-isoquinolinecarboxylate To a suspension of 33 g (3.05 equiv) of aluminum chloride in 180 mL of dichloroethane was added, under N$_2$, at room temperature, a solution containing 20 g of (−)-eserethole in 20 mL of dichloroethane over 25 minutes. The resulting dark homogeneous mixture was heated under reflux for 1-2 hours (or until complete disappearance of (−)-eserethole). The reaction was cooled to ∼15° C. and then poured into a stirred mixture of 300 g of ice and 100 mL of concentrated hydrochloric acid. The 2-phase mixture was filtered through Celite ® diatomaceous earth and rinsed with 100 mL of 3N hydrochloric acid. The 2-phases were separated. The aqueous phase (which contained (−)-eseroline) was cooled to 15° C., and then basified, under N$_2$, with 152 mL of 45% potassium hydroxide solution, while maintaining the temperature under 20° C., to pH 6–7. A solution containing 39 g of L-tartaric acid in 50 mL of water was added. The pH of the reaction mixture was brought to 6–7 by the addition of 40 mL of a 50% potassium carbonate solution. To this mixture was then added 200 mL of ethyl acetate, and the mixture was further basified to 9–9.5 by the addition of 55 mL of 50% potassium carbonate solution. The 2 phases were separated and the aqueous mixture was extracted with 200 mL of ethyl acetate. The combined ethyl acetate solution was dried with 40 g of anhydrous potassium carbonate and filtered under N$_2$.

To the ethyl acetate solution (which contained (−)-eseroline) was added, under N$_2$, 13.17 g (1.0 equiv) of 1,1′-carbonyldiimidazole, as a solid, in several portions. This was followed by the addition of 13.16 g (3.0 equiv) of glacial acid and 10.81 g (1.07 equiv) of 1,2,3,4-tetrahydroisoquinoline in 20 mL of ethyl acetate. After stirring overnight, the reaction mixture was extracted with 200 mL of water. The ethyl acetate solution was further extracted twice with 100 mL of 0.5N sodium hydroxide solution, and 100 mL of water. After drying over anhydrous sodium sulfate, the ethyl acetate solution was concentrated under reduced pressure to give 24.66 g (80.5%) of crude product.

EXAMPLE 2

The de-ethylation of (−)-eserethole was carried out substantially as described in Example 1. (−)-Eseroline was isolated using ethylenediaminetetraacetic acid tetrasodium salt dihydrate instead of L-tartaric acid.

EXAMPLE 3

(3aS-cis)-1,2,3,3a,8,8a-Hexahydro-1,3a,8-trimethylpyrrolo[2,3-b]-indol-5-yl 3,4-dihydro-2(1H)-isoquinolinecarboxylate To a suspension of 0.825 kg (3.05 equiv) of aluminum chloride in 4.5 L of dichloroethane was added, under N$_2$, at room temperature, a solution containing 0.5 kg of (−)-eserethole in 0.5 L of dichloroethane over 30 minutes. The resulting dark homogeneous mixture was heated at 70–75° C. for 2–3 hours (or until complete disappearance of (−)-eserethole). The reaction was cooled to ∼15° C. and then poured into a stirred mixture of 7.5 kg of ice and 2.5 L of 37% hydrochloric acid. The 2 phase mixture was filtered through Celite ® and rinsed with 2.5 L of 3N hydrochloric acid. The 2 phases were separated. The aqueous phase (which contained (−)-eseroline) was cooled to ∼10° C., and then basified, under N$_2$, with ∼4 L of 45% potassium hydroxide solution, while maintaining the temperature under 15° C., to pH 6–7. A solution containing 0.938 kg of L-tartaric acid in 1.25 L of water was added. The pH of the reaction mixture was brought to ∼5 by the addition of 0.93 L of a 50% potassium carbonate solution. To this mixture was then added 5 L of ethyl acetate, and the mixture was further basified to 8.5 by the addition of 2.4 L of 50% potassium carbonate solution. The 2 phases were separated and the aqueous mixture was extracted with 5 L of ethyl acetate. The combined ethyl acetate solution was dried with 1.55 kg of anhydrous potassium carbonate, filtered under N$_2$, and the filter cake rinsed with 1 L of ethyl acetate.

To the ethyl acetate solution (which contained (−)-eseroline) was added, under N$_2$, 0.312 kg (0.95 equiv) of 1,1′-carbonyldiimidazole, as a solid, in several portions. The reaction mixture was cooled, and 0.347 kg (2.84 equiv) of glacial acetic acid was added. This was followed by the addition of 0.270 kg (1.0 equiv) of 1,2,3,4-tetrahydroisoquinoline in 0.25 L of ethyl acetate. After stirring overnight, the reaction mixture was extracted with 2.5 L of water. The 2 phases were separated, and the aqueous phase was extracted with 0.75 L of ethyl acetate. The combined ethyl acetate solution was further extracted twice with 2.5 L of 0.5N sodium hydroxide solution, and 2.5 L of water. After drying over 2 kg of anhydrous potassium carbonate, the mixture was filtered and the filter cake was washed with 1 L of ethyl acetate.

The ethyl acetate solution was treated with 0.07 kg of Norit, and filtered through Celite ®. The Celite ® cake was washed with 0.66 L of ethyl acetate. The filtrate was then concentrated under reduced pressure to give 0.489 kg (75.6%) of crude product which was further purified by chromatography on silica gel (2.44 kg, ethyl acetate as eluent), followed by recrystallization from 0.5 L of cyclohexane, to give 0.344 kg (54.6%) of pure produce.

EXAMPLE 4

To a suspension of 4.27 g of aluminum chloride in 200 mL of dichloroethane was added under $N_2$, a solution containing 25 g of (−)-eserethole. The resulting mixture was heated under reflux until complete reaction. The reaction mixture was quenched into a mixture of 300 g of ice and 200 mL of 3N HCl. The biphasic mixture was filtered through Celite ®, and the phases were separated. The aqueous phase was slowly basified under $N_2$ to pH 6 resulting in a very thick paste. To this suspension was added 200 mL of water, and the mixture was then centrifuged at 1200 rpm for 30 minutes. 400 mL of this aqueous mixture was decanted off, basified with potassium carbonate and extracted with methylene chloride. HPLC assay of this solution suggested ≦50% of eseroline was isolated.

EXAMPLE 5

(3aS-cis)-1,2,3,3a,8,8a-hexahydro-1,3a,8-trimethylpyrrolo]2,3-b]-indol-5-ol, cyclohexyl carbamate ester To a solution of (−)-eseroline (2.2 g) obtained substantially as described in Example 10, there is added benzene (50 mL) containing cyclohexyl isocyanate (1.2 g) and the mixture is stirred at 25° C. for 3 hours. The product is isolated followed substantially the procedure described in Example 1.

EXAMPLE 6

(3aS-cis)-1,2,3,3a,8,8a-hexahydro-1,3a,8-trimethylpyrrolo[2,3-b]-indol-5-ol, 3-chlorophenyl carbamate ester fumarate To a solution of (−)-eseroline (2.2 g) obtained substantially as described in Example 10, there is added 3-chlorophenyl isocyanate (1.5 g) over 1 hour at 5° C. and the mixture is stirred at 25° C. for 3 hours. The product is isolated as the fumarate salt following water washing, concentration under reduced pressure, chromatographic purification on silica gel with ethyl acetate, and acidification of the purified free base in ethyl acetate with fumaric acid (1 equiv).

EXAMPLE 7

(3aS-cis)-1,2,3,3a,8,8a-hexahydro-1,3a,8-trimethylpyrrolo[2,3-b]-indol-5-ol, 3-chlorophenyl carbamate ester To a dichloroethane solution (−)-eseroline, (2.2 g) prepared following substantially the procedure described in Example 10, there is added 3-chlorophenyl isocyanate (1.6 g) at −5° C. over 5 minutes. After stirring for 0.25 hour the product, (3aS-cis)-1,2,3,3a,8,8a-hexahydro-1,3a,8-trimethylpyrrolo[2,3-b]-indol-5-ol, 3-chlorophenyl carbamate ester, is isolated substantially as described in Example 1.

EXAMPLE 8

(3a,S-cis)-[3aα,5(R*),8aα-1,2,3,3a,8,8a-hexahydro-1,3a,8-trimethylpyrrolo[2,3-b]-indol-5-ol, 1-(phenyl)ethyl carbamate ester To a solution of (−)-eseroline (2.2 g) prepared following substantially the procedure described in Example 10 there is added (S)-(−)-α-methylbenzyl isocyanate (1.5 g) over 1.5 hours at 10° C. The resulting product is isolated substantially as described in Example 1 and recrystallized from diisopropyl ether.

EXAMPLE 9

(3aS-cis)-[3aα,5(S*),8aα]]-1,2,3,3a,8,8a-hexahydro-1,3a,8-trimethyl-pyrrolo[2,3-b]-indol-5-ol, 1-(phenyl)ethyl carbamate ester To a solution of (−)-eseroline (2.2 g) obtained substantially as described in Example 10, was added (R)(+)-α-methylbenzyl isocyanate (1.5 g) is added over 0.5 hour at 10° C. The product is isolated following water washing, concentration of the organic phase and chromatographic purification on neutral alumina with DCM elution and recrystallization from diisopropyl ether.

EXAMPLE 10

(3aS-cis)-1,2,3,3a,8,8a-Hexahydro-1,3a,8-trimethylpyrrolo[2,3-b]-indol-5-yl 3,4-dihydro-2(1H)-isoquinolinecarboxylate To a suspension of 33 g (3.05 equiv) of aluminum chloride in 180 mL of dichloroethane was added, under $N_2$, at room temperature, a solution containing 20 g of (−)-eserethole in 20 mL of dichloroethane over 5 minutes. The resulting dark homogeneous mixture was heated under $N_2$ at ~75° C. for 1.5 hours (or until complete disappearance of (−)-eserethole). The reaction was cooled to ~15° C. and then poured into a stirred mixture of 300 g of ice and 100 mL of water. The suspension was basified, under $N_2$, with ~45 mL of 45° potassium hydroxide solution, while maintaining the temperature under 20° C., to pH 6–7. A solution containing 39 g of L-tartaric acid in 50 mL of water was added. The pH of the reaction mixture was brought to 8 by the addition of 50 mL of 45% potassium carbonate solution. The 2 phases were separated and the aqueous mixture was extracted with 100 mL of dichloroethane. The combined dichloroethane solution was dried with 40 g of anhydrous potassium carbonate and filtered under $N_2$, and the filter cake rinsed with 50 mL of dichloroethane.

To the dichloroethane solution (which contained (−)-eseroline) was added, under $N_2$, 13.2 g (1.0 equiv) of 1,1'-carbonyldiimidazole, as a solid, in one portion. The reaction mixture was cooled in an ice-bath. This was followed by the addition of 13.2 g (3.0 equiv) of glacial acetic acid and 10.8 g (1.07 equiv) of 1,2,3,4-tetrahydroisoquinoline. After stirring overnight, the reaction mixture was washed with 200 mL of water, 200 mL of 0.5N sodium hydroxide solution, and then 200 mL of water. After drying over anhydrous potassium carbonate or 4 Angstrom molecular sieves, the dichloroethane solution was concentrated under reduced pressure to give 26.53 g (87%) of crude product. The crude material was chromatrographed on silica gel, eluting with ethyl acetate. After concentrating, the residue was dissolved in 250 mL of cyclohexane, and slurried with 2.6 g of Norit. The suspension was filtered through Celite®, and the Celite® cake washed with 25 mL of cyclohexane. The filtrate was concentrated and the residue was recrystallized from cyclohexane to give 15.09 g (49%) of pure product.

EXAMPLE 11

(+)-cis-1,2,3,3a,8,8a-Hexahydro-1,3a,8-trimethylpyrrolo[2,3-b]-indol-5-yl 3,4-dihydro-2(1H)-isoquinolinecarboxylate To a stirred solution containing 10.72 g of (+)-eserethole in 250 mL of $CH_2Cl_2$ at 0°–5° C. was added, under $N_2$, a solution containing 12.5 mL of $BBr_3$ in 25 ml of $CH_2Cl_2$ over 30 min. After 1–2 h, the reaction mixture was quenched with 2 mL of MeOH, followed by 120 mL of a $K_2CO_3$ solution (100 g/300 mL $H_2O$), and 50 mL of $H_2O$. The pH of the mixture was further adjusted to pH 9 by the addition of 40 mL of the $K_2CO_3$ solution. The phases were separated and the aqueous solution was extracted with 100 mL of $CH_2Cl_2$. The combined $CH_2Cl_2$ solutions were dried ($Na_2SO_4$) and then filtered under $N_2$.

To the above filtrate was added 6.35 g of 1,1'-carbonyldiimidazole. The reaction mixture was stirred for 1 h under $N_2$, and then cooled to 0°–5° C.

To the cooled reaction mixture was added 6.75 mL of acetic acid followed by 5.98 g of 1,2,3,4-tetrahydroisoquinoline. The reaction mixture was allowed to warm to room temperature and stirred overnight. The mixture was extracted with 5% $NaHCO_3$(1×100 mL), $H_2O$ (2×100 mL), dried ($Na_2SO_4$), and concentrated under reduced pressure. The crude oil was chromatrographed on $SiO_2$ (6% MeOH/EtOAc). Pure (±)-cis-1,2,3,3a,8,8a-hexahydro-1,3a,8-trimethylpyrrolo[2,3-b]indol-5-yl 3,4-dihydro-2(1H)-isoquinolinecarboxylate, mp 117.5°–119° C., was obtained as a white solid in 60% yield after recrystallization from 4:1 MeOH/$H_2O$ and cyclohexane.

EXAMPLE 12

(3aS)-cis-1,2,3,3a,8,8a-Hexahydro-1,3a,8-trimethylpyrrolo[2,3-b]-indol-5-yl 3,4-dihydro-2(1H)-isoquinolinecarboxylate To a suspension of aluminum chloride (2.06–2.17 kg) in 1,2-dichloroethane (11.25 L) is added, under $N_2$, a solution containing (−)-eserethole (1.25 kg) in 1,2-dichloroethane (1.25 L) over 10–40 minutes. The resulting dark mixture is heated under $N_2$ at 70°–82° C. for 1–3 hours. The reaction is cooled to 10°–30° C. and then poured into a stirred mixture of ice water. The suspension is basified, under $N_2$, with a 50% sodium hydroxide solution and a 50% potassium carbonate solution, while maintaining the temperature under 20° C., to pH 8.5–9.5, and then filtered. The phases are separated and the aqueous phase is extracted with 1,2-dichloroethane. The combined 1,2-dichloroethane solution is dried with anhydrous potassium carbonate, filtered under $N_2$, and then used directly in the next step.

To the above 1,2-dichloroethane filtrate is added, under $N_2$ and at ambient temperature, 1,1'-carbonyldiimidazole (0.741–0.905 kg, 1.0–1.1 equiv.). The reaction solution is stirred for 1–2 hours. This solution is used directly in the next step.

Acetic acid (0.305–1.007 kg, 1.0–3.3 equiv) and 1,2,3,4-tetrahydroisoquinoline (0.676–0.811 kg, 1.0–1.2 equiv) are then sequentially added while maintaining the temperature below 30° C. After stirring overnight, the reaction mixture is washed with water, 0.5N sodium hydroxide solution, and then water. The organic phase is dried over anhydrous potassium carbonate or 4 Angstrom molecular sieves and them concentrated under reduced pressure to yield crude product. This crude material is chromatrographed on silica gel eluting with ethyl acetate. The fractions containing the product are combined and concentrated under reduced pressure. Residual ethyl acetate is azeotropically removed by diluting the concentrated with cyclohexane and then reconcentrating under reduce pressure to yield the desired product. The purified product, (3aS-cis)-1,2,3,3a,8,8a-hexahydro-1,3a,8-trimethylpyrrolo[2,3-b]indol-5-yl 3,4-dihydro-2(1H)-isoquinolinecarboxylate is obtained, in 40–69% yield, after recrystallizing from cyclohexane and drying under reduced pressure.

It is to be understood that this method is effective for chiral as well as racemic compounds and that such changes and variations may be made without departing from the spirit and scope of the invention as defined by the appended claims.

We claim:

1. A process for the preparation of a product of the formula

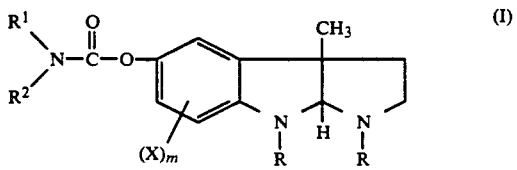

wherein

R is lower alkyl;

$R^1$ is hydrogen, loweralkyl, lowercycloalkyl, lowercycloalkylloweralkyl, lowerbicycloalkyl, aryl or arylloweralkyl;

X is loweralkyl, loweralkoxy; halogen or trifluoromethyl; and m is 0, 1 or 2;

which process comprises (a) contacting a compound of Formula II

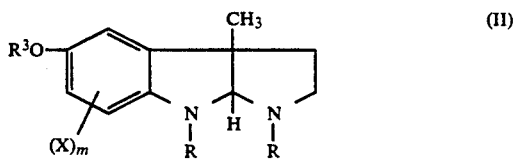

wherein R, X and m are as defined above and $R^3$ is loweralkyl, with a reagent selective from the group consisting of aluminum chloride, hydrobromic acid and boron tribromide followed by tartaric acid to afford a compound of Formula III

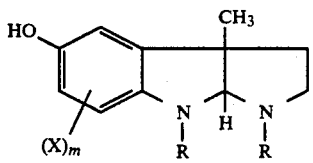 (III)

wherein R, X and m are as defined above;

(b) contacting the reaction mixture containing compound of Formula III with an isocyanate of the formula $R^1NCO$ and isolating a product of the Formula I.

2. The process of claim 1 wherein the reagent employed in step (a) is aluminum chloride.

3. The process of claim 1 wherein a reaction solvent is employed.

4. The process of claim 3 wherein the solvent is dichloroethane.

5. The process of claim 1 wherein the pH of the reaction medium of step (a) is adjusted to a value within the range of about 5 to about 10 by addition of a base.

6. The process of claim 2 wherein the base is potassium hydroxide or potassium chloride.

7. The process of claim 6 wherein the pH is within the range of about 8 to about 9.

8. The process of claim 1 wherein the pH of the reaction medium of step (b) is adjusted to a value within the range of about 4.0 to about 13.0.

9. The process of claim 8 wherein the pH is within the range of about 9 to about 10.

10. The process of claim 9 wherein the pH is about 5.2.

11. The process of claim 1 wherein R and $R^3$ of the starting material is loweralkyl and X is hydrogen.

12. The process of claim 11 wherein R is methyl and $R^3$ is methyl or ethyl.

13. The process of claim 1 wherein R is methyl and $R^3$ is a methyl.

14. The process of claim 12 wherein the starting material is (−)-eserethole.

* * * * *